US00PP28665P3

(12) United States Plant Patent
NeSmith

(10) Patent No.: US PP28,665 P3
(45) Date of Patent: Nov. 21, 2017

(54) DWARF HYBRID BLUEBERRY PLANT NAMED 'TO-1319'

(50) Latin Name: *Vaccinium corymbosum*
Varietal Denomination: TO-1319

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 52 days.

(21) Appl. No.: 14/998,663

(22) Filed: Jan. 28, 2016

(65) Prior Publication Data

US 2017/0223883 P1 Aug. 3, 2017

(51) Int. Cl.
*A01H 5/08* (2006.01)

(52) U.S. Cl.
USPC ..... Plt./157

(58) Field of Classification Search
USPC ..... Plt./157
CPC ..... A01H 5/08; A01H 5/00
See application file for complete search history.

(56) References Cited

PUBLICATIONS

NeSmith Ornamental Blueberry Variety Development at the University of Georgia A Progress Report for 2012, retrieved on Apr. 26, 2017, retrieved from the Internet at http://www.smallfruits.org/blueberries/production/OrnamentalReport2012.pdf pp. 1-16.*

* cited by examiner

*Primary Examiner* — June Hwu
(74) *Attorney, Agent, or Firm* — Klarquist Sparkman, LLP

(57) ABSTRACT

The new variety 'TO-1319' has fruit that ripens around late May in southern Georgia and mid-late June in middle Georgia. The fruit of the new variety 'TO-1319' are light-blue, medium size, and firm, with a mild flavor. The new variety 'TO-1319' is vigorous with an estimated chilling requirement of about 400 to 500 hours at or below approximately 45° C.

4 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TO-1319' is an ultra dwarf hybrid blueberry plant known as southern highbush (*Vaccinium corymbosum*).

Variety denomination: The new ultra dwarf hybrid ornamental blueberry plant claimed is of the variety denominated 'TO-1319'.

BACKGROUND OF THE INVENTION

The present invention relates to the discovery of a new and distinct cultivar of dwarf hybrid blueberry plant botanically known as *Vaccinium corymbosum* and herein referred to as 'TO-1319', as herein described and illustrated.

The new blueberry plant variety 'TO-1319' was selected in Griffin, Ga. in 2007. The new variety 'TO-1319' ripens around late May in southern Georgia. The fruit of the new variety 'TO-1319' are medium sized and are light-blue. The new variety 'TO-1319' has good yield for a dwarf type blueberry plant and is vigorous with an estimated chilling requirement of about 400-500 hours at or below 45° F.

Pedigree and history: 'TO-1319' was selected in 2007 at the Georgia Experiment Station in Griffin, Ga., originating from a cross of 'Rebel' (U.S. Plant Pat. No. 18,138) made in 2007 with 'TH-639' (a non-patented breeding line). The selection was first asexually propagated by softwood cuttings at the direction of the inventor in Griffin, Ga. in 2009. The new variety has been tested in plantings at UGA Blueberry Research Farms in Alapaha and Griffin, Ga. since 2010. The selection was planted in ornamental trials at the Alapaha and Griffin, Ga. locations in 2011.

SUMMARY OF THE INVENTION

The new blueberry plant variety 'TO-1319' has not been observed under all possible environmental conditions. The phenotype may vary somewhat with variations in environment and cultural practices such as temperature and light intensity without, however, any variance in genotype.

The following traits have been repeatedly observed in asexually propagated plants of the new variety growing in Alapaha and Griffin Ga., and are determined to be the unique characteristics of the new blueberry plant variety 'TO-1319':

1. Good crop load;
2. Ultra dwarf or compact plant;
3. Medium berry size;
4. Well suited for home gardeners, landscapes, and container production.

The new variety 'TO-1319' can be compared to the variety 'Rebel' (the subject of U.S. Plant Pat. No. 18,138) and southern highbush blueberry variety 'Camellia' (the subject of U.S. Plant Pat. No. 18,151).

Comparison The selection flowers and ripens at a time that is in between the ripening of 'Rebel' and the late season variety 'Camellia' in the late Georgia southern highbush season. 'TO-1319' has medium size, light-blue berries and typically has a good crop load as compared to 'Rebel' and 'Camellia' in Alapaha and Griffin, Ga. over a 2-year period (Tables 1 and 2). 'TO-1319' plants are very compact/dwarfed, but are vigorous, being well suited for home gardeners, landscapes, and container production. Unlike the dwarfed characteristic of 'TO-1319', both 'Rebel' and 'TH-639' are normal sized blueberry plants. 'TO-1319' also has a smaller berry size than 'Rebel'.

Major attractions of 'TO-1319' are its ornamental appeal, robustness, and suitability for home garden, container production, and landscape use. 'TO-1319' has self-fruitfulness typical for southern highbush varieties. No notable diseases or other pest problems have been observed for the new variety that are not also common for other varieties.

TABLE 1

2-year average ratings of some fruit and plant characteristics of ornamental 'TO-1319' and standard commercial cultivars 'Rebel' and 'Camellia' (2013-2014) in field test plots at Alapaha, GA. Rating scales are based on a 1 to 10 score, with 1 being the least desirable and 10 being the most desirable. These plants were established in 2011.

| | Alapaha Location | | |
|---|---|---|---|
| Berry and Plant Attributes | 'Rebel' | 'Camellia' | 'TO-1319' |
| Berry size | 8.2 | 8.8 | 7.2 |
| Berry scar | 7.3 | 7.0 | 7.0 |
| Berry color | 7.5 | 8.3 | 7.2 |
| Berry firmness | 7.2 | 7.2 | 7.0 |
| Berry flavor | 6.5 | 7.5 | 7.0 |
| Cropping | 5.5 | 6.0 | 5.5 |
| Plant vigor | 7.5 | 9.5 | 7.0 |
| Date of 50% flowering | March 1 | March 13 | March 8 |
| Date of 50% ripening | May 8 | May 21 | May 13 |
| Fruit development period (days) | 68 | 69 | 66 |

TABLE 2

2-year average ratings of some fruit and plant characteristics of ornamental 'TO-1319' and standard commercial cultivars 'Rebel' and 'Camellia' (2013-2014) in field test plots at Griffin, GA. Rating scales are based on a 1 to 10 score, with 1 being the least desirable and 10 being the most desirable. These plants were established in 2011.

| | Griffin location | | |
|---|---|---|---|
| Berry and Plant Attributes | 'Rebel' | 'Camellia' | 'TO-1319' |
| Berry size | 7.0 | 8.8 | 7.0 |
| Berry scar | 7.0 | 7.0 | 7.0 |
| Berry color | 7.0 | 8.3 | 7.0 |
| Berry firmness | 7.0 | 7.2 | 7.0 |
| Berry flavor | 6.3 | 7.2 | 6.8 |
| Cropping | 6.0 | 6.5 | 5.0 |
| Plant vigor | 6.5 | 8.5 | 7.3 |
| Date of 50% flowering | March 14 | March 27 | March 20 |
| Date of 50% ripening | May 25 | June 6 | May 29 |
| Fruit development period (days) | 72 | 71 | 70 |

BRIEF DESCRIPTION OF THE FIGURES

The accompanying photographic illustrations show typical specimens in full color of the foliage, flowering, and fruit of the new variety 'TO-1319'. The colors are as nearly true as is reasonably possible in a color representation of this type. The plants in the FIGS. are three year old plants.

BOTANICAL DESCRIPTION

Figure 1:
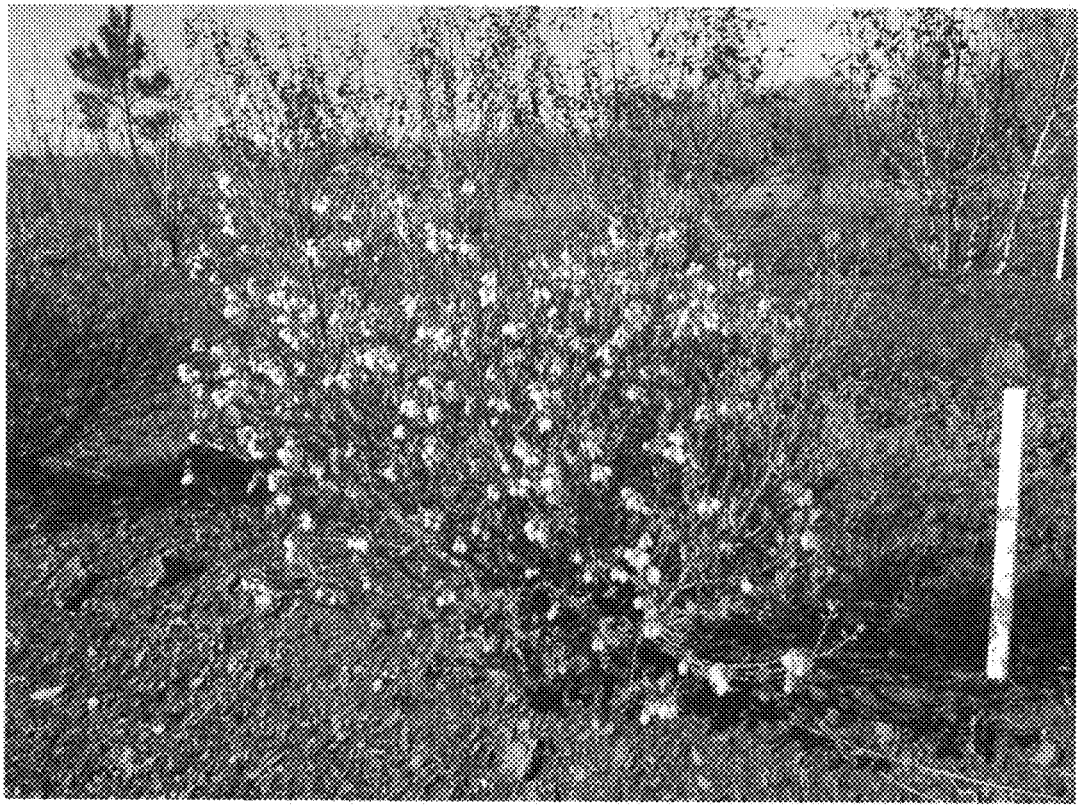
FIG. 1 contains a photograph of the new variety 'TO-1319' plants during flowering in Alapaha, Ga.
Figure 2:
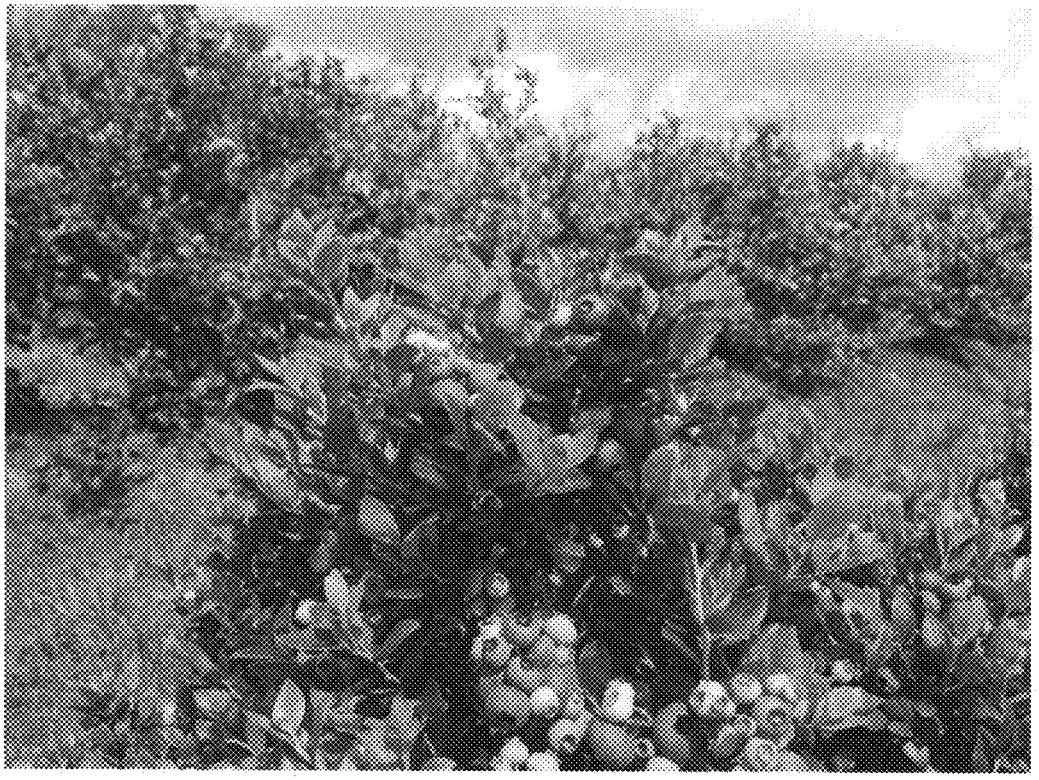
FIG. 2 is a close up photograph of the new variety 'TO-1319' during fruit ripening in Alapaha, Ga.
Figure 3A:
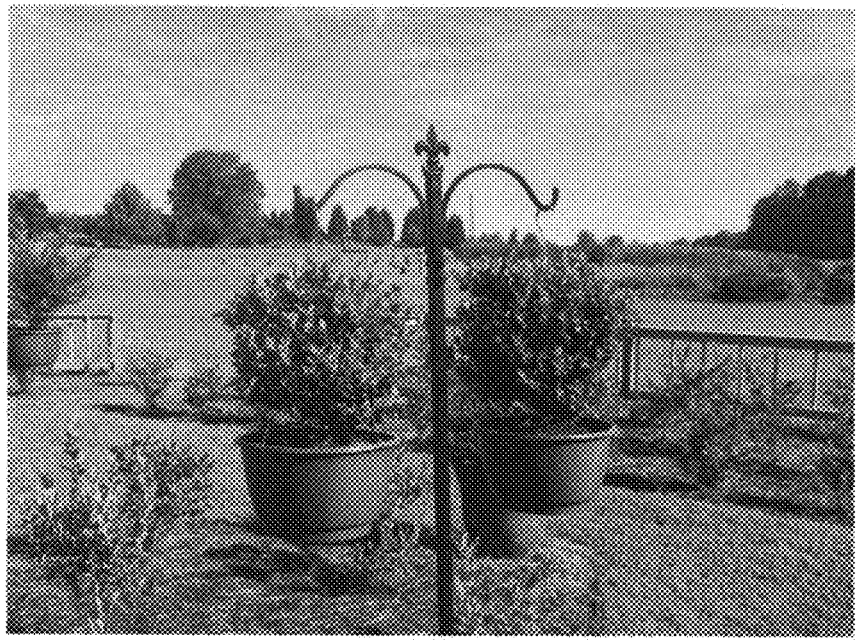
FIGS. 3A and 3B contain photographs of new variety 'TO-1319' as container grown plants.
Figure 3B:
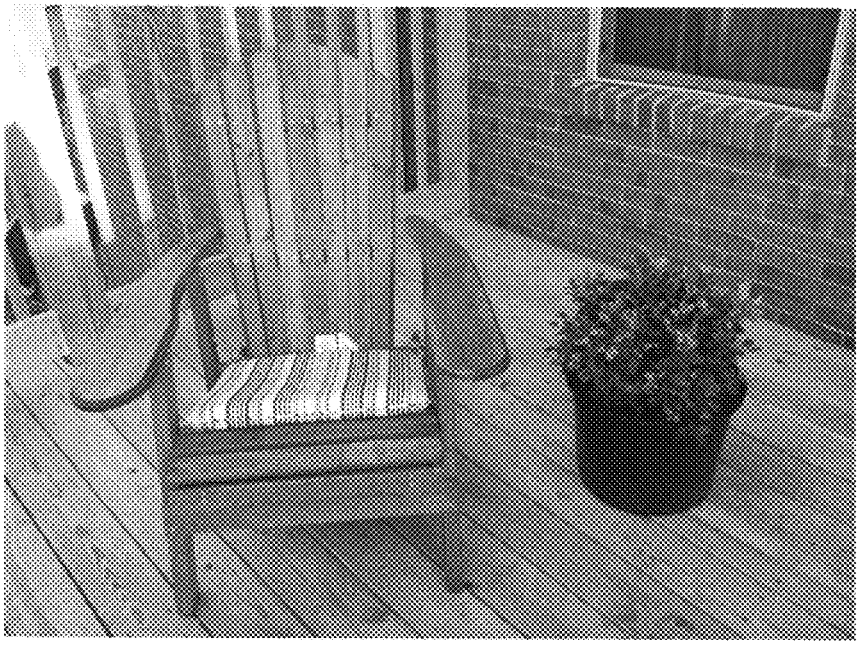
Figure 4:
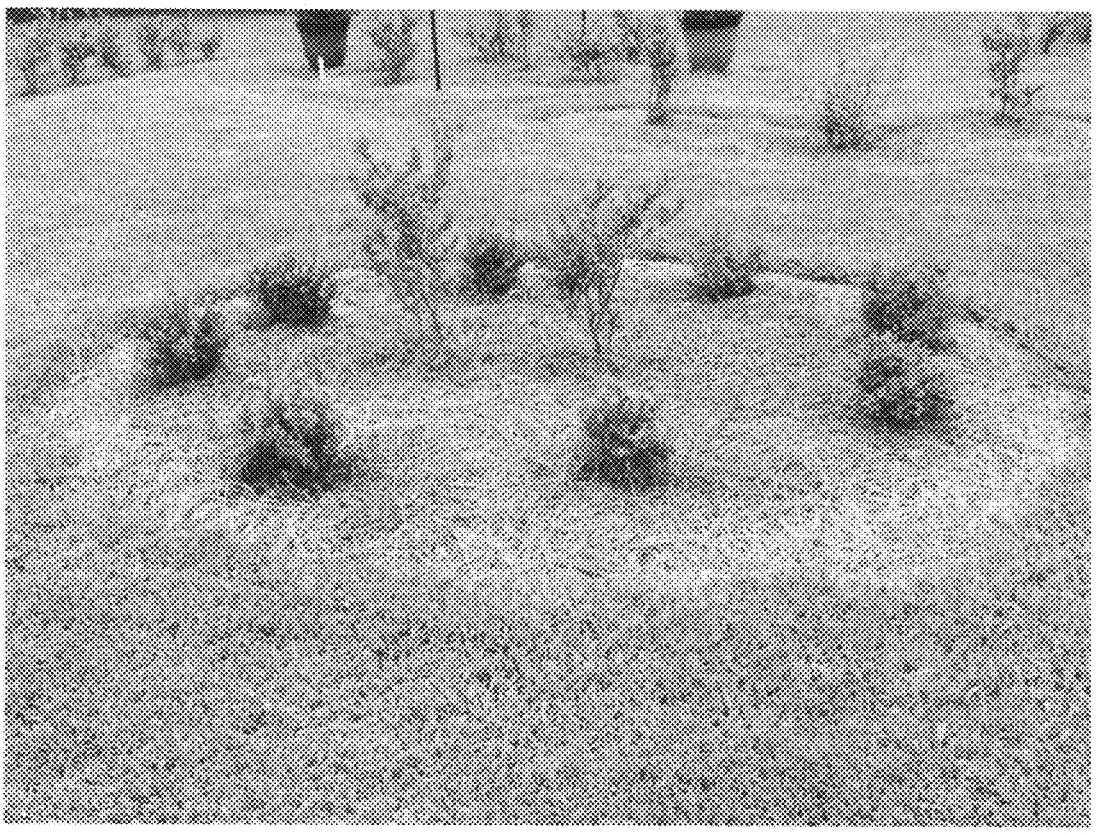
FIG. 4 is a photograph of new variety 'TO-1319' being used to accent a landscape as ground cover.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following is a detailed description of the botanical and pomological characteristics of the new variety 'TO-1319'. Where dimensions, sizes, colors, and other characteristics are given, it is to be understood that such characteristics are approximations and averages set forth as accurately as practicable. The descriptions reported herein are largely from specimen plants grown in Alapaha and Griffin, Ga., with supplemental irrigation. Plants were about 4 to about 6 years old.

PLANT

Size: 30 to 40 cm tall by 4 years. The plant crown, or base, is narrow, typically less than 10 cm in diameter. Upper portion of plant canopy can reach 45 to 60 cm in diameter by 4 years.

Growth habit: Strongly dwarf, very compact with 6 to 8 main canes arising from the crown at the soil surface. Over abundance of branching throughout the plant makes a very dense canopy.

Growth: Moderately vigorous, but can grow poorly in overly wet soil condition. Plant is highly fitting for container production in a suitable organic media.

Productivity: Even though this is an ultra-dwarf ornamental blueberry, where yield is not relevant, fruit set or cropping is high to very high under ideal conditions. Annual yields of 1 to 3 lbs per plant on plants 4 years old is not unusual.

Hardiness: Similar to other varieties such as Rebel and 'Camellia'.

Chilling requirement: 400-500 hour of temperatures at or below 7° C. (about 45° F.) to induce normal leafing and flowering during the spring.

Leafing: Plants readily break numerous leaf buds simultaneous with anthesis.

Canes:

*Diameter.*—10 to 15 mm for base of main canes that are about 4 years old and older; 8-10 mm first major branch diameter; 4 to 6 mm in about 2 year old wood; 2 to 4 mm in current season wood.

*Color.*—Most mixture Grey Brown RHS 199C and RHS N199B for base of canes that are about 4 years old and older; most near Grey Brown RHS 199C for first major branch. Yellow Green RHS 146B rapidly transitioning to Grey Brown RHS 199D in about 2 year old wood. Yellow Green RHS 144A to RHS 146B in current season wood.

Fruiting wood: Numerous twigs 8 to 10 cm in length, with internode lengths of 2 to 5 mm common.

Disease resistance: No exceptional disease resistance or susceptibility observed; similar to 'Rebel' and 'Camellia'.

FOLIAGE

Leaf color: Healthy mature leaves.
*Top side.*—Yellow Green RHS 146A to 146B.
*Under side.*—Green RHS 139D.
Leaf arrangement: Alternate, simple.
Leaf shape: Elliptic.
Leaf surfaces: Both upper and lower leaf surfaces are glaucous.
Leaf margins: Nearly entire, slightly crenate.
Leaf venation: Pinnate, with high degree of netting.
Leaf apices: Broadly acute.
Leaf bases: Acute.
Leaf dimensions:
*Length.*—30.0 to 35.0 mm.
*Width.*—15.0 to 20.0 mm.
Petioles: Small.
*Length.*—1.0 to 1.5 mm.
*Width.*—0.5 to 1.0 mm.
*Color.*—Yellow-Green RHS 145A.

FLOWERS

Vegetative burst: Early, occasionally simultaneously or just after flowering.
Date of 50% anthesis: March 8 in southern Georgia and March 20 in middle Georgia (2 year average).
Flower shape: Urceolate.
Flower bud: Number: Very high, averaging 10 or more buds per fruiting shoot; flower bud anthocyanin coloration is weak.
Flowers per cluster: 5 to 7 common.
Flower fragrance: Slight "freshly cut grass" fragrance.
Corolla:
*Color.*—White RHS 155C.
*Length.*—7.5 to 9.0 mm.
*Width.*—5.5 to 6.5 mm.
*Aperture width.*—2.5 to 3.0 mm.
Flower peduncle:
*Length.*—6.0 to 8.0 mm.
*Color.*—Green RHS 138D.
Flower inflorescence: Made up of the peduncle and the corolla having respective sizes as indicated above.
Flower pedicel:
*Length.*—3.0 to 4.0 mm.
*Color.*—Primarily Green RHS 138D, with some Red Purple RHS 63B streaks.
Calyx (with sepals):
*Diameter.*—5.0 to 6.0 mm.
*Color.*—Green RHS 138C.
Stamen:
*Length.*—5.5 to 6.0 mm.
*Number per flower.*—10.
*Filament color.*—Yellow-Green RHS 145D.
Style:
*Length.*—7.5 to 8.5 mm.
*Color.*—Yellow-Green RHS 145C.
Pistil:
*Length.*—9.5 to 10.5 mm.
*Ovary color* (*exterior*).—Green RHS 138C.
Anther:
*Length.*—3.5 to 4.0 mm.
*Number.*—10.
*Color.*—Greyed-Orange RHS 164A.
Pollen:
*Abundance.*—Medium.
*Color.*—Yellow-White RHS 158A.
Self-compatibility: The cultivar has a moderate degree of self-compatibility.

FRUIT

Date of 50% maturity: May 13 in southern Georgia and May 29 in middle Georgia (2 year average).
Fruit development period: 65 to 70 days. Fruiting on one year old shoots, not found on current season wood in most circumstances.
Berry color:
*With wax.*—Violet Blue RHS 97C.
*Without wax.*—Black RHS 202A.
Berry surface wax abundance: High.
Fruit bloom intensity: Moderate to strong.
Berry flesh color: White RHS 155C.
Berry weight:
*First harvest.*—1.7 g to 2.3 g.
*Second harvest.*—1.4 g to 1.8 g.
Berry size:
*Height from calyx to scar.*—9.0 to 13.0 mm.
*Diameter.*—10.0 to 15.0 mm.
Berry shape: Semi-spherical.
Fruit stem scar: Medium, dry, with little tearing at harvest.
Calyx: Depth 3.0 to 4.0 mm; width 4.0 to 5.0 mm; sepals outward when present.
Berry firmness: Medium firm.
Berry flavor and texture: Mild flavor, not very sweet, not very acidic; smooth texture.
Storage quality: Medium.
Suitability for mechanical harvesting: Not suitable.
Uses: Intended for home gardens, container gardening, and/or ornamental uses.

SEED

Seed abundance in fruit: Medium, with 10-20 fully developed seeds per berry.
Seed color: Greyed-Orange RHS 165A to 165B.
Seed dry weight: 42.5 mg per 100 seeds.
Seed size: 1.2 to 1.6 mm long; 0.3 to 0.6 mm wide for fully developed seeds.

What is claimed is:

1. A new and distinct dwarf variety of hybrid blueberry plant, as herein illustrated and described.

* * * * *